US00PP29583P2

(12) United States Plant Patent
O'Connell

(10) Patent No.: US PP29,583 P2
(45) Date of Patent: Aug. 7, 2018

(54) ***AEONIUM* PLANT NAMED 'BLACK RUBY'**

(50) Latin Name: *Aeonium hybrida*
Varietal Denomination: Black Ruby

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,165

(22) Filed: Apr. 26, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Aeonium* cultivar named 'Black Ruby' is disclosed, characterized by dense clusters of deep red/bronze rosettes, with green centers. Plants offset in multiple rings, abundantly and early, as well as distinctively low on the plant, forming even, attractive plants. Plants are more robust and grow more rapidly than typical of *Aeonium*. *Aeonium* is typically produced as a plant for the patio containers or for landscape use.

1 Drawing Sheet

Latin name of the genus and species: *Aeonium hybrida*.
Variety denomination: 'BLACK RUBY'.

BACKGROUND OF THE INVENTION

The new cultivar, *Aeonium* 'Black Ruby', was found by the inventor, Renee O'Connell, as the result of a crossing made February 2013 as part of a planned breeding program. The seed parent variety is the unpatented proprietary variety referred to as *Aeonium hybrida* 'CAT1'. The pollen parent is the unpatented variety *Aeonium hybrida* '13'. *Aeonium* 'Black Ruby' was selected by the inventor, Renee O Connell, in October of 2013 from a group of seedlings resulting from the February crossing, at a commercial greenhouse in Vista. Calif.

Asexual reproduction of the new cultivar 'Black Ruby' was first performed in Vista, Calif., at a commercial greenhouse, by vegetative off-sets in Spring of 2014. 'Black Ruby' has since produced multiple generations and has shown that the unique features of this cultivar are stable and reproduced true to type.

SUMMARY OF THE INVENTION

The cultivar 'BLACK RUBY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLACK RUBY' These characteristics in combination distinguish 'BLACK RUBY' as a new and distinct *Aeonium* cultivar:

1. Unique deep red/bronze foliage with green immature centers.
2. *Aeonium* 'Black Ruby' freely produces branching at a small size and at an early age, a characteristic not exhibited by many other comparable *Aeoniums*.

3. *Aeonium* 'Black Ruby', exhibits enhanced production times as the early and free production of offsets fills the designated pot size much more rapidly than many other comparable *Aeoniums*.
4. *Aeonium* 'Black Ruby' combines rapid growth and robustness, in tandem with early, free offsetting, a combination not exhibited by many other comparable *Aeoniums*.
5. *Aeonium* 'Black Ruby', with maturity will grow to 18"-24" diameter, with a height of approximately 12" to 15"
6. *Aeonium* 'Black Ruby', produces multiple rings of offsets, creating a very full, attractive cluster.

PARENTAL COMPARISON

Plants of the new cultivar 'BLACK RUBY' are similar to plants of the seed parent in most horticultural characteristics, however, plants of the new cultivar 'BLACK RUBY' differ in the following;

1. *Aeonium* 'Black Ruby' exhibits a desirable wine-red color, not exhibited by the *Aeonium* 'CAT 1'.
2. *Aeonium* 'CAT 1', while it does offset, does not offset as low to the ground nor as freely as does *Aeonium* 'Black Ruby'.
3. *Aeonium* 'Black Ruby' grows more rapidly and robustly than does *Aeonium* 'CAT 1'.
4. *Aeonium* 'Black Ruby' forms a more aesthetically balanced cluster than does *Aeonium* 'CAT 1' due to the formation of offsets at a lower height on the plant and the production of profuse offsets.

Plants of the new cultivar 'BLACK RUBY' are similar to plants of the pollen parent in most horticultural characteristics, however, plants of the new cultivar 'BLACK RUBY' differ in the following;

1. *Aeonium* 'Black Ruby' varies from the pollen parent in that it freely produces offsets at a young age and at a low height on the plant, whereas *Aeonium* '13' produces occasional offsets at a much older age.

2. *Aeonium* 'Black Ruby' exhibits significantly more deep red/bronze color than does the pollen parent *Aeonium* '13'.
3. *Aeonium* 'Black Ruby' produces a well-balanced, aesthetically attractive cluster, whereas the pollen parent *Aeonium* '13' has a sparser, uneven morphology that is not as attractive.

COMMERCIAL COMPARISON

Plants of the new cultivar 'BLACK RUBY' are comparable to the well-known unpatented, commercial variety *Aeonium* 'Zwartkop'. The two *Aeonium* varieties are similar in most horticultural characteristics; however, the new variety 'BLACK RUBY' differs in the following:

1. *Aeonium* hybrid 'Black Ruby' produces red/bronze foliage whereas *Aeonium* 'Zwartkop' produces nearly black foliage.
2. *Aeonium* 'Black Ruby' exhibits early offsetting whereas *Aeonium* 'Zwartdop' produces offsets at an older age.
3. *Aeonium* 'Black Ruby' begins to offset at a plant height of approximately 6", whereas *Aeonium* 'Zwartkop' generally tends to produce offsets when the plant is 12" or more in height.
4. Due to the profuse and low offsetting tendencies expressed by *Aeonium* 'Black Ruby', a much more aesthetically balanced plant is produced as compared to *Aeonium* 'Zwartkop'.
5. *Aeonium* 'Black Ruby' forms multiple rings of offsets, with a concentric morphology; attributes not expressed by *Aeonium* 'Zwartkop'.
6. *Aeonium* 'Black Ruby' forms clusters that are 18" to 24" in diameter and 12" to 15" in height, whereas *Aeonium* 'Zwartkop' grows to 3' to 4' in height.

Plants of the new cultivar 'BLACK RUBY' can also be comparable to the unpatented commercial variety *Aeonium* 'Party Platter'. The two *Aeonium* varieties are similar in most horticultural characteristics; however, the new variety 'BLACK RUBY' differs in the following:

1. *Aeonium* 'Black Ruby' produces red/bronze foliage whereas the foliage of *Aeonium* 'Party Platter' is lime green.
2. *Aeonium* 'Black Ruby' is heavy offsetting, as is *Aeonium* hybrid 'Party Platter', but *Aeonium* 'Black Ruby', due to its somewhat taller stature, can be used more readily in the landscape where a mid-height plant is desired than can *Aeonium* hybrid 'Party Platter'.
3. *Aeonium* 'Black Ruby' produces a more upright cluster, than does *Aeonium* 'Party Platter', which forms a much shorter, flatter cluster.

BRIEF DESCRIPTION OF THE PHOTOGRAPH

The accompanying photograph illustrates in full color a typical of plant of *Aeonium* 'Black Ruby' grown in a shade house in Vista, Calif. at a light intensity of approximately 2500 to 3500 fc. Age of the plant photographed is approximately 10 months from a rooted plantlet. The photograph was taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural Society Colour Chart, 2007, except where general terms of ordinary dictionary significance are used. The following observations and measurements describe 'Black Ruby' plants in a commercial shade house in Vista, Calif. Temperatures ranged from approximately 1° C. to 38° C. night and day. No artificial light, photoperiodic treatments or chemical treatments were given to the plants. Natural light conditions were approximately 2500 to 3500 fc of light. Measurements and numerical values represent averages of typical plant types.

Botanical classification: *Aeonium hybrida* 'BLACK RUBY'.

PROPAGATION

Type of propagation typically used: Vegetative offsets.

Time to initiate roots: About 18 days at approximately 24° C.

Root description: Fibrous, brown, not accurately measured with a color chart.

PLANT

Age of plant described: Approximately 4 months.

Container size of the plant described: 1 gallon.

Growth habit: Upright, caulescent, with a terminal rosette, very freely offsetting. Rosette somewhat upwardly cupped.

Height: Approximately 25 cm to top of highest leaf.

Plant spread: 38 cm.

Growth rate: Moderately fast.

Branching characteristics: Freely offsetting.

Rosettes per plant: Average range 12 to 20.

FOLIAGE

Leaf:

*Arrangement*.—Rosulate.

*Average length*.—Outer rosette mature leaf approximately 12 cm. Inner rosette mature leaf approximately 5.5 cm.

*Average width*.—2.5 to 3.5 cm.

*Width at base*.—1.2 cm.

*Shape of blade*.—Spatulate.

*Apex*.—Mucronate and blunt rounded. Immature aspices more founded, mature foliage slightly more angular.

*Base*.—Cuneate.

*Margin*.—Finely ciliate.

*Texture of top surface*.—Glabrous.

*Texture of bottom surface*.—Glabrous.

*Quantity of leaves per rosette*.—Average range 50 to 80.

*Color*.—Young foliage upper side: Base Yellow-Green 144D. Mid-section near Green 138B, uppermost section Green 137A. Apical margin 187B. Young foliage, under side: Base Yellow-Green 144D. Mid-section near Green 138B, uppermost section Green 137B. Apical margin 187B. Mature foliage upper side: Base Yellow-Green 144D. Mid-section Green 138B almost entirely covered in deep flush N186C and N187A. Uppermost section N186C and N187A. Apical margin 187B. Mature foliage, under side: Base Yellow-Green 144D. Mid-section Green 138B almost entirely covered in deep flush N186C and N187A. Uppermost section N186C and N187A. Apical margin 187B.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered or produced fruits and seeds to date.

Temperature tolerance: Tolerates temperatures from approximately −2 degrees C. to 40 degrees C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'BLACK RUBY' as herein illustrated and described.

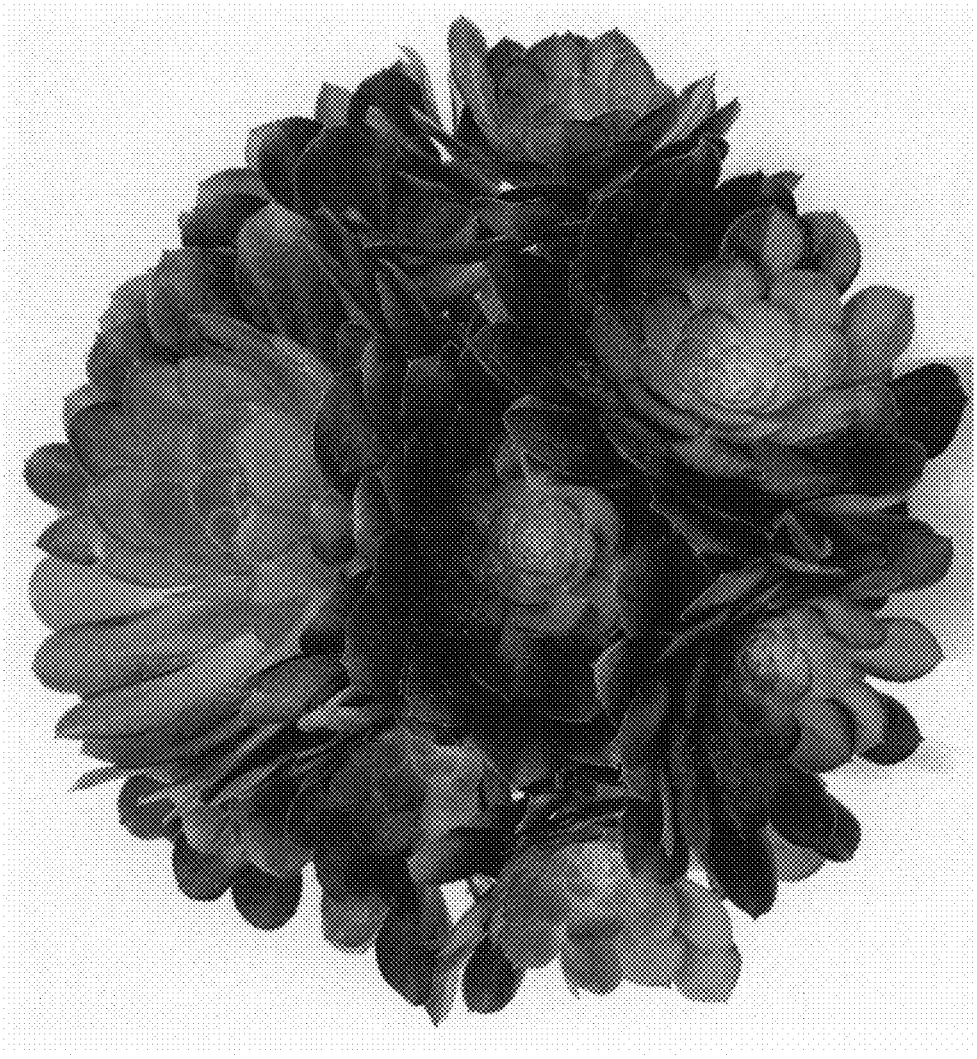

* * * * *